(12) United States Patent
Evangelista et al.

(10) Patent No.: US 7,297,555 B2
(45) Date of Patent: Nov. 20, 2007

(54) HYDROPHILIC CHEMILUMINESCENT ACRIDINIUM LABELING REAGENTS

(75) Inventors: Ramon Evangelista, Laguna Hills, CA (US); Martha Garrity, San Clemente, CA (US)

(73) Assignee: Quest Diagnostics Investments Incorporated, Wilmington, DE (US)

(*) Notice: Subject to any disclaimer, the term of this patent is extended or adjusted under 35 U.S.C. 154(b) by 75 days.

(21) Appl. No.: 11/181,531

(22) Filed: Jul. 14, 2005

(65) Prior Publication Data

US 2005/0255528 A1    Nov. 17, 2005

Related U.S. Application Data

(62) Division of application No. 10/225,084, filed on Aug. 20, 2002, now Pat. No. 6,924,154.

(51) Int. Cl.
| | | |
|---|---|---|
| G01N 33/533 | (2006.01) | |
| G01N 33/532 | (2006.01) | |
| G01N 21/76 | (2006.01) | |
| G01N 33/53 | (2006.01) | |
| C07D 219/02 | (2006.01) | |
| C07D 219/04 | (2006.01) | |

(52) U.S. Cl. .................. 436/546; 436/544; 436/172; 436/800; 435/7.1; 435/968; 546/102; 546/104

(58) Field of Classification Search ............... 546/104; 544/335, 405; 436/526, 546, 544, 172, 800; 435/7.5, 7.1, 968
See application file for complete search history.

(56) References Cited

U.S. PATENT DOCUMENTS

| | | |
|---|---|---|
| 3,964,870 A | 6/1976 | Tiedemann et al. |
| 4,220,450 A | 9/1980 | Maggio |
| 4,226,993 A | 10/1980 | Buckler et al. |

(Continued)

FOREIGN PATENT DOCUMENTS

CA    2319187    6/2000

(Continued)

OTHER PUBLICATIONS

S. Zalipsky, Bioconjugate Chemistry, vol. 5, pp. 150-165 (1995). Functionalized Poly(ethylene glycol) for Preparation of Biologically Relevant Conjugates.*

(Continued)

*Primary Examiner*—Long V. Le
*Assistant Examiner*—Shafiqul Haq
(74) *Attorney, Agent, or Firm*—Foley & Lardner, LLP (57) ABSTRACT

In accordance with the present invention, it has been discovered that introduction of hydrophilic sulfoalkyl substituents and/or hydrophilic linkers derived from homocysteic acid, cysteic acid, glycine peptides, tetraethylene oxide, and the like, offset the hydrophobicity of the acridinium ring system to produce a more soluble label which can be attached to an antibody at higher loading before precipitation and aggregation problems are encountered. Additional compounds described herein contain linkers derived from short peptides and tetraethylene oxide which increase aqueous solubility due to hydrogen bonding with water molecules. The present invention also embraces reagents for multiple acridinium labeling for signal amplification composed of a peptide bearing several acridinium esters with sulfonate groups at regularly spaced intervals for increased solubility. The invention also embraces assays employing the above-described compounds.

17 Claims, 6 Drawing Sheets

U.S. PATENT DOCUMENTS

| | | |
|---|---|---|
| 4,277,437 A | 7/1981 | Maggio |
| 4,380,580 A | 4/1983 | Boguslaski et al. |
| 4,383,031 A | 5/1983 | Boguslaski et al. |
| 4,427,770 A | 1/1984 | Chen et al. |
| 4,652,533 A | 3/1987 | Jolley |
| 5,110,932 A | 5/1992 | Law et al. |
| 5,281,712 A | 1/1994 | McCapra et al. |
| 5,283,334 A | 2/1994 | McCapra |
| 5,284,951 A | 2/1994 | McCapra et al. |
| 5,284,952 A | 2/1994 | Ramakrishnan |
| 5,321,136 A | 6/1994 | McCapra |

FOREIGN PATENT DOCUMENTS

| | | |
|---|---|---|
| WO | WO96/13612 | 5/1996 |
| WO | WO98/54574 | 12/1998 |
| WO | WO 00/31543 | 6/2000 |

OTHER PUBLICATIONS

International Search Report for PCT Application No. PCT/US03/25922, Jul. 14, 2005.

Supplementary European Search Report for European Application No. EP 03 79 3122, Sep. 28, 2004.

* cited by examiner

HYDROPHILIC CHEMILUMINESCENT ACRIDINIUM LABELING REAGENTS

CROSS-REFERENCE TO RELATED PATENT APPLICATIONS

This application is a Division of U.S. application Ser. No. 10/225,084, filed Aug. 20, 2002, now U.S. Pat. No. 6,924,154 and incorporated herein by reference in its entirety.

FIELD OF THE INVENTION

The present invention relates to amine-reactive acridinium labeling reagents. In a particular aspect, the present invention relates to acridinium labeling reagents having one or more hydrophilic substituents thereon. In another aspect, the present invention relates to conjugates containing invention acridinium labeling reagents, kits containing same, and assays employing same.

BACKGROUND OF THE INVENTION

The following description of the background of the invention is provided simply as an aid in understanding the invention and is not admitted to describe or constitute prior art to the invention.

Chemiluminescence immunoassays which employ acridinium labels have advantages of high throughput and high analytical sensitivity for low-level analytes of clinical significance. Usually it is desirable to use labeled antibodies with a large number of chemiluminescent tags, which produce high luminescence counts, which, in turn, allows one to achieve lower detection limits. This holds true provided that non-specific binding can be minimized.

During conjugation of antibodies with presently available labeling reagents at relatively high reagent-to-protein ratios, low recoveries of the labeled proteins are often obtained. In most of these labeling reactions, protein precipitation and/or formation of protein aggregates have been observed. Presumably, the precipitates and aggregates are the result of protein molecules with higher degree of labeling than the immunologically active conjugates, which remain in solution. The tendency towards precipitation and aggregation can be attributed to the hydrophobic nature of the four-ring aromatic acridinium ester label.

Accordingly, there is a need in the art for acridinium labeling reagents which have a reduced propensity to cause protein precipitation and/or promote formation of protein aggregates.

BRIEF DESCRIPTION OF THE INVENTION

In accordance with the present invention, it has been discovered that introduction of hydrophilic sulfoalkyl substituents and/or hydrophilic linkers derived from homocysteic acid, cysteic acid, glycine peptides, tetraethylene oxide, and the like, offset the hydrophobicity of the acridinium ring system to produce a more soluble label which can be attached to an antibody at higher loading before precipitation and aggregation problems are encountered.

Additional compounds described herein contain linkers derived from short peptides and tetraethylene oxide which increase aqueous solubility due to hydrogen bonding with water molecules. The present invention also embraces reagents for multiple acridinium labeling for signal amplification composed of a peptide bearing several acridinium esters with sulfonate groups at regularly spaced intervals for increased solubility.

In accordance with another aspect of the present invention, there are provided assays for the presence of an analyte in a sample, said assay comprising:

contacting an analyte with an invention conjugate,
inducing chemiluminescence by decay of an intermediate formable in the presence of a peroxide or molecular oxygen, and
measuring chemiluminescence therefrom to assay the analyte.

In accordance with still another aspect of the present invention, there are provided improved diagnostic assays for the detection of an analyte using a chemiluminescent label conjugated to a specific binding material, the improvement comprising employing an invention compound as the chemiluminescent label compound.

The summary of the invention described above is not limiting and other features and advantages of the invention will be apparent from the following detailed description of the preferred embodiments, as well as from the claims.

BRIEF DESCRIPTION OF THE FIGURES

FIG. 5 provides reaction schemes describing the formation of exemplary acridinium-protein conjugates using NHS esters (FIG. 5a) and pentafluorophenyl esters (FIG. 5b) according to the invention.

DETAILED DESCRIPTION OF THE INVENTION

In accordance with the present invention, there are provided chemiluminescent compounds having the structure:

wherein:
X=O, S or NR', wherein R' is H or alkyl or substituted alkyl;
Y=O or S;
Z=alkyl, sulfoalkyl, alkenyl, or sulfoalkenyl;
Ar=aryl or heteroaryl bearing at least one —SO$_2$L substituent, wherein L is halogen or NHQ, wherein Q is a linker bearing an amine reactive group;
R=sulfoalkyl or sulfoalkenyl;
A$^-$ is an optional suitable counter-ion; and
n=0-3;
provided that if L is halogen, Z is sulfoalkyl or sulfoalkenyl.

Figure 1:
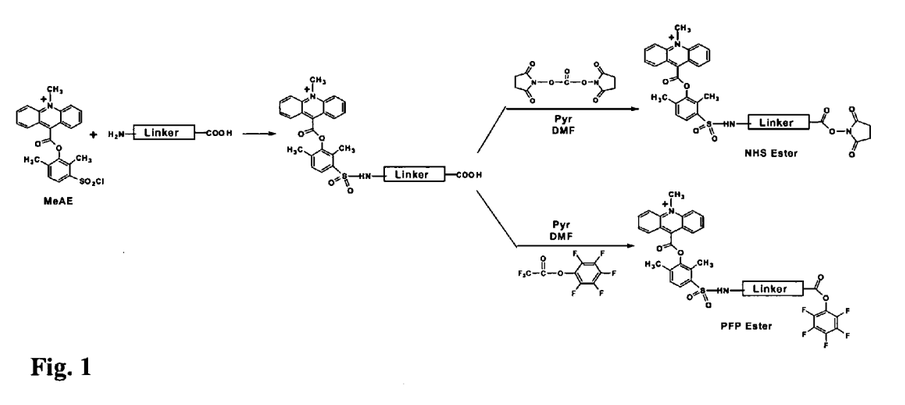
FIG. 1 provides a reaction scheme for preparation of exemplary hydrophilic chemiluminescent compounds according to the invention, useful as labeling reagents.

Thus, in one aspect of the present invention, there are provided amine-reactive acridinium labeling reagents comprising: 1) a chemiluminescent acridinium ester, 2) a hydrophilic substituent such as a sulfoalkyl group and/or a hydrophilic linker such as those derived from a sulfonated amino acid such as cysteic acid or homocysteic acid or a short peptide such as diglycine, triglycine or tetraglycine or a peptide containing cysteic acid or homocysteic acid with multiple acridinium labels or a linker containing tetraethylene oxide and 3) a reactive group such as sulfonyl chloride, succinimidyl ester (NHS ester) or pentafluorophenyl ester. A variety of structures and commonly used designations therefor, together with the prior art chemiluminescent reagent, MeAE, are shown in FIG. 1.

As employed herein, "alkyl" refers to saturated straight or branched chain hydrocarbon radical having in the range of 1 up to about 20 carbon atoms. "Lower alkyl" refers to alkyl groups having in the range of 1 up to about 5 carbon atoms. "Substituted alkyl" refers to alkyl groups further bearing one or more substituents selected from hydroxy, alkoxy (of a lower alkyl group), mercapto (of a lower alkyl group), cycloalkyl, substituted cycloalkyl, heterocyclic, substituted heterocyclic, aryl, substituted aryl, heteroaryl, substituted heteroaryl, aryloxy, substituted aryloxy, halogen, trifluoromethyl, cyano, nitro, nitrone, amino, amido, —C(O)H, acyl, oxyacyl, carboxyl, carbamate, dithiocarbamoyl, sulfonyl, sulfonamide, sulfuryl, and the like.

As used herein, "sulfoalkyl" refers to substituents having the structure:

wherein:
each R" is independently H, lower alkyl, substituted lower alkyl; and
q=1-6.

Thus, the term sulfoalkyl embraces such groups as sulfomethyl, sulfoethyl, sulfopropyl, sulfobutyl, sulfopentyl, sulfohexyl, and the like. A presently preferred sulfoalkyl group according to the invention is sulfopropyl.

As used herein, "sulfoalkenyl" refers to substituents having the structure:

wherein:
each R" is independently H, lower alkyl, substituted lower alkyl; and
each r is independently 0-4.

Thus, the term sulfoalkenyl embraces such groups as sulfoethenyl, sulfopropenyl, sulfobutenyl, sulfopentenyl, sulfohexenyl, and the like. A presently preferred sulfoalkenyl group according to the invention is sulfopropenyl.

As employed herein, "aryl" refers to aromatic groups having in the range of 6 up to 14 carbon atoms and "substituted aryl" refers to aryl groups further bearing one or more substituents as set forth above. In one aspect of the invention, aryl is a 2,6-dialkyl substituted phenyl, such as, for example, 2,6-dimethylphenyl, 2,6-diethylphenyl, and the like. A presently preferred aryl contemplated for use in the practice of the present invention is a group having the structure In accordance with another preferred aspect of the present invention, Ar has the structure:

wherein Q is polyoxyalkylene, poly-L-lysine, poly-(lysine-homocysteic acid), poly-(lysine-cysteic acid), polyglycine, aminodextran, or the like.

As employed herein, "heteroaryl" refers to aromatic groups having in the range of 4 up to about 13 carbon atoms, and at least one heteroatom selected from O, N, S, or the like; and "substituted heteroaryl" refers to heteroaryl groups further bearing one or more substituents as set forth above. Exemplary heteroaryl compounds contemplated for use in the practice of the present invention include pyridyl, pyrimidyl, pyrazinyl, triazolyl, isooxazolyl, isothioazolyl, imidazolyl, and the like.

As employed herein, "halogen" refers to fluoride, chloride, bromide or iodide atoms.

As employed herein, "suitable counter-ion", A⁻, refers to halogen ions, sulfate ions, nitrate ions, carboxylate ions, triflate ions, fluoroslufonate ions, difluorosulfonate ions, and the like. The use of a counter-ion is optional, in that certain molecules may use an internal "counter-ion"; for example, when Z is sulfoalkyl or sulfoalkenyl, the sulfo-moiety provides a suitable counter-ion.

Linkers bearing an amine reactive group, Q, contemplated for use in the practice of the present invention include succinimidyl esters (e.g., N-hydroxysuccinimide esters or NHS esters), N-hydroxyphthalimide esters, pentafluorophenyl esters, tetrafluorophenyl esters, 2-nitrophenyl esters, 4-nitrophenyl esters, dichlorotriazines, isothiocyanates, and the like.

In one aspect of the invention, compounds wherein X is O are presently preferred. In another aspect of the present invention, compounds wherein Y is O are also preferred. In a particularly preferred aspect of the invention, both X and Y are O.

Exemplary compounds contemplated by the present invention include compounds wherein:
X is O,
Y is O,
Z is sulfoalkyl,
Ar is 2,6-dimethyl-3- or 4-chlorosulfophenyl,
R is not present,
A⁻ not present, and
n is 0.

Especially preferred compounds are those having the above-described substitution pattern and wherein Z is sulfopropyl. Additional preferred compounds are those wherein Ar is 2,6-dimethyl-3-chlorosulfophenyl or 2,6-dimethyl-4-chlorosulfophenyl.

Figure 6:
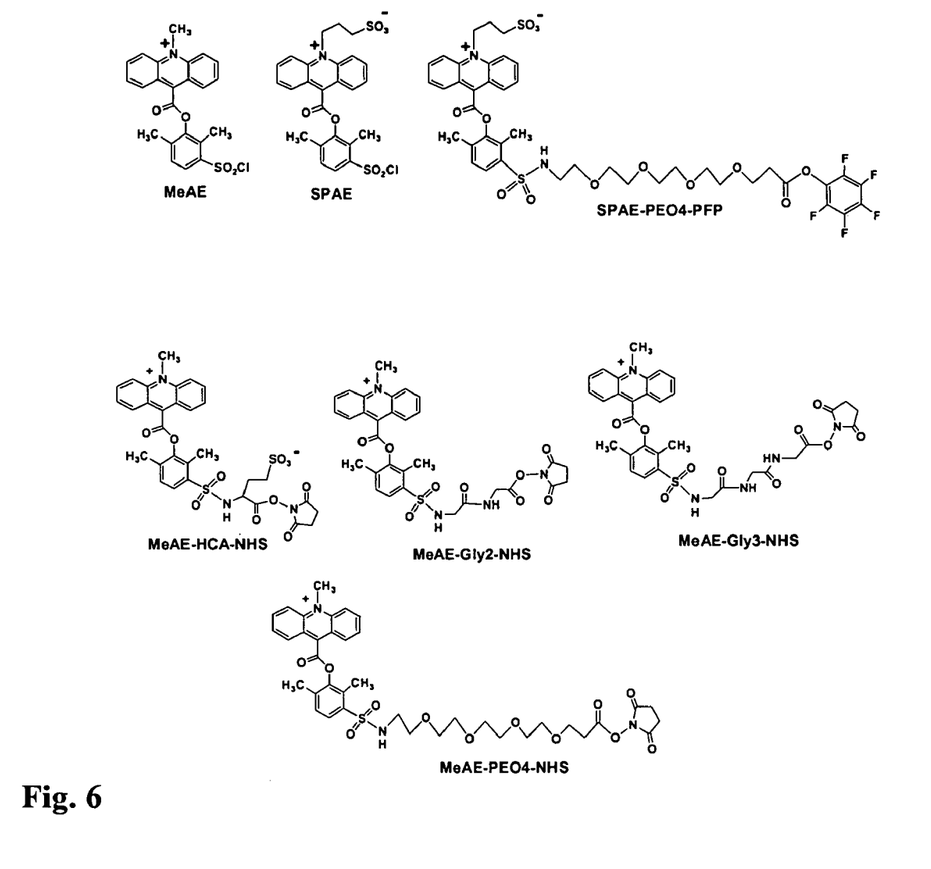
FIG. 6 presents the chemical structures of several acridinium labeling reagents (e.g., MeAE and SPAE derivatives).

Additional exemplary compounds according to the present invention are set forth in FIG. 6, e.g., 2,6-(dimethyl)-3-chlorosulfonylphenyl-N-(3-sulfopropyl)-acridinium-9-carboxylate ("SPAE"), SPAE-(polyethyleneoxide)₄-pentafluorophenyl ester ("SPAE-PEO4-PFP"), 2,6-(dimethyl)-3-chlorosulfonylphenyl-N-methyl-acridinium-9-carboxylate triflate ("MeAE"), and MeAE-(polyethylene oxide)₄-N-hydroxysuccinimide ester ("MeAE-PEO4-NHS").

In accordance with another aspect of the present invention, there are provided chemiluminescent conjugates comprising a chemiluminescent compound as described herein, conjugated with a specific binding material.

"Specific binding material" means herein any material which will bind specifically by an immunoreaction, protein binding reaction, nucleic acid hybridization reaction, and any other reaction in which the material reacts specifically with a restricted class of biological, biochemical or chemical species. Specific binding materials contemplated for use in the practice of the present invention include antibodies, enzymes and substrates therefor, antibodies and antigens therefor, avidin-biotin, nucleic acids, and the like.

Invention chemiluminescent compounds are useful in a broad range of specific binding assays for the presence of analyte in a sample. "Presence" shall mean herein the qualitative and/or quantitative detection of an analyte. Such assays may be directed at any analyte which may be detected by use of the improved chemiluminescent compound in conjunction with specific binding reactions to form a moiety thereon. These assays include, without limitation, immunoassays, protein binding assays and nucleic acid hybridization assays.

In a typical immunoassay, the analyte is immunoreactive and its presence in a sample may be determined by virtue of its immunoreaction with an assay reagent. In a typical protein binding assay, the presence of analyte in a sample is determined by the specific binding reactivity of the analyte with an assay reagent where the reactivity is other than immunoreactivity. Examples of alternative specific binding reactions for use in assays include enzyme-substrate recognition and the binding affinity of avidin for biotin. In the typical nucleic acid hybridization assay, the presence of analyte in a sample is determined by a hybridization reaction of the analyte with an assay reagent. Analyte nucleic acid (usually present as double stranded DNA or RNA) is usually first converted to a single stranded form and immobilized onto a carrier (e.g., nitrocellulose paper). The analyte nucleic acid may alternatively be electrophoresed into a gel matrix. The immobilized analyte may then be hybridized (i.e., specifically bound) by a complementary sequence of nucleic acid.

The foregoing specific binding assays may be performed in a wide variety of assay formats. These assay formats fall within two broad categories. In the first category, the assay utilizes an invention chemiluminescent conjugate which comprises a chemiluminescent moiety of the invention attached to a specific binding material. In this category of assays, the invention chemiluminescent conjugate participates in a specific binding reaction and the presence of analyte in the sample is proportional to the formation of one or more specific binding reaction products containing the invention chemiluminescent conjugate. The assay is performed by allowing the requisite specific binding reactions to occur under suitable reaction conditions. The formation of specific binding reaction products containing the invention chemiluminescent conjugate is determined by measuring the chemiluminescence of such products containing the invention chemiluminescent conjugate or by measuring the chemiluminescence of unreacted or partially reacted invention chemiluminescent conjugate not contained in such products.

This first category of assay formats is illustrated by sandwich assays, competitive assays, surface antigen assays, sequential saturation assays, competitive displacement assays and quenching assays.

In a sandwich format, the specific binding material to which the chemiluminescent moiety is attached is capable of specifically binding with an analyte of interest. The assay further utilizes a reactant which is capable of specifically binding with the analyte to form a reactant-analyte-chemiluminescent conjugate complex. The reactant may be attached to a solid phase, including without limitation, dip sticks, beads, tubes, paper, polymer sheets, and the like. In such cases, the presence of analyte in a sample will be proportional to the chemiluminescence of the solid phase after the specific binding reactions are completed. Such assay formats are discussed further in U.S. Pat. Nos. 4,652, 533, 4,383,031, 4,380,580 and 4,226,993, which are incorporated herein by reference in their entirety, including all figures, tables, and claims.

In a competitive format, the assay utilizes a reactant which is capable of specifically binding with the analyte to form an analyte-reactant complex and with the specific binding material, to which a chemiluminescent moiety of the invention is attached, to form a chemiluminescent conjugate-reactant complex. The reactant may be attached to a solid phase, or alternatively reaction products containing the reactant may be precipitated by use of a second antibody or by other known means. In this competitive format, the presence of analyte is "proportional," i.e., inversely proportional, to the chemiluminescence of the solid phase or precipitate. A further discussion of this assay format may be found in the immediately above mentioned U.S. patents.

In another assay format, the analyte may occur on or be bound to a larger biological, biochemical or chemical species. This type of format is illustrated by a surface antigen assay. In this format, the specific binding material is capable of specifically binding with the analyte and the presence of analyte is proportional to the analyte-chemiluminescent conjugate complex formed as a reaction product. This is illustrated by attaching a chemiluminescent moiety of the invention to an antibody which is specific to a surface antigen on a cell. The presence of the cell surface antigen will be indicated by the chemiluminescence of the cells after the completion of the reaction. The cells themselves may be used in conjunction with a filtration system to separate the analyte-chemiluminescent conjugate complex which is formed on the surface of the cell from unreacted chemiluminescent conjugate. This is discussed further in U.S. Pat. No. 4,652,533.

Chemiluminescent moieties of the invention may be used in additional assay formats known in the art including without limitation sequential saturation and competitive displacement, both of which utilize a chemiluminescent conjugate where both (1) the specific binding material, to which the moiety is attached, and (2) the analyte, specifically bind with a reactant. In the case of sequential saturation, the analyte is reacted with the reactant first, followed by reaction of the chemiluminescent conjugate with the remaining unreacted reactant. In the case of competitive displacement, the chemiluminescent conjugate competitively displaces analyte which has already bound to the reactant.

In a quenching format, the assay utilizes a reactant which is capable of specifically binding with (i) the analyte to form an analyte-reactant complex, and (ii) with the specific binding material to which the chemiluminescent moiety is attached to form a chemiluminescent conjugate-reactant complex. A quenching moiety is attached to the reactant. When brought into close proximity to the chemiluminescent moiety, the quenching moiety reduces or quenches the chemiluminescence of the chemiluminescent moiety. In this quenching format, the presence of analyte is proportional to the chemiluminescence of the chemiluminescent moiety. A further discussion of this format may be found in U.S. Pat. Nos. 4,220,450 and 4,277,437, which are incorporated herein by reference in their entirety, including all figures, tables, and claims.

In consideration of the above discussed assay formats, and in the formats to be discussed below, the order in which assay reagents are added and reacted may vary widely as is well known in the art. For example, in a sandwich assay, the reactant bound to a solid phase may be reacted with an analyte contained in a sample and after this reaction the solid phase containing complexed analyte may be separated from the remaining sample. After this separation step, the chemiluminescent conjugate may be reacted with the complex on the solid phase. Alternatively, the solid phase, sample and chemiluminescent conjugate may be added together simultaneously and reacted prior to separation. As a still further alternative, the analyte in the sample and the chemiluminescent conjugate may be reacted prior to addition of the reactant on the solid phase. Similar variations in the mixing and reaction steps are possible for competitive assay formats as well as other formats known in the art. "Allowing under suitable conditions substantial formation" of specific binding reaction products shall herein include the many different variations on the order of addition and reaction of assay reagents.

In the second category of assay formats, the assay utilizes an unconjugated chemiluminescent compound of the invention. The presence of analyte in the sample is proportional to the formation of one or more specific binding reaction products which do not themselves contain the chemiluminescent moiety. Instead, the chemiluminescent compound chemiluminesces in proportion to the formation of such reaction products.

In one example of this second category of assays, the assay utilizes a reactant capable of binding with the analyte to form an analyte-reactant complex which causes the chemiluminescent compound to chemiluminesce. This is illustrated by a simple enzyme-substrate assay in which the analyte is the substrate glucose and the reactant is the enzyme glucose oxidase. Formation of the enzyme-substrate complex triggers the chemiluminescent compound. Such enzyme-substrate assay for glucose is disclosed in U.S. Pat. Nos. 3,964,870 and 4,427,770, which are incorporated herein by reference in their entirety, including all figures, tables, and claims. This enzyme-substrate assay is a specific binding assay in the sense that the substrate specifically binds to the active site of the enzyme in much the same way that an antigen binds to an antibody. In this assay, the enzyme specifically binds with the substrate which results in the production of peroxide which, in turn, causes the chemiluminescent compound to chemiluminesce.

Also included in the second category of assays are those assays in which the formation of the reaction products promotes or inhibits chemiluminescence by the chemiluminescent compound in a less direct manner. In this assay, a first reactant, which is cross reactive with the analyte, is attached to an enzyme such as glucose oxidase close to its active site: A second reactant which is specific for both the analyte and the immunoreactive material is added to the sample and the altered enzyme in the presence of the substrate (i.e., glucose). When the second reactant binds to the first reactant located near the active site on the enzyme, the second reactant blocks the active site in a way that the substrate cannot bind to the enzyme at the active site, or the binding of the substrate at the active site is significantly decreased. The second reactant blocking the enzyme in this manner inhibits the enzyme from producing peroxide which, in turn, would have triggered the chemiluminescent moiety. Analyte in the sample, however, will tie up the second reactant, thus preventing the second reactant from inhibiting the production of peroxide. The presence of analyte will be proportional to the chemiluminescence of the compound.

The assays contained in the above two categories of assay formats may be heterogeneous or homogeneous. In heterogeneous assays, the reaction products, whose formation is proportional to the presence of analyte in the sample, are separated from other products of the reaction. Separation can be achieved by any means, including without limitation, separation of a liquid phase from a solid phase by filtration, microfiltration, double antibody precipitation, centrifugation, size exclusion chromatography, removal of a solid phase (e.g., a dip stick) from a sample solution or electrophoresis. For example, in a sandwich assay the reactant-analyte-chemiluminescent conjugate complex is separated from unreacted chemiluminescent conjugate. In a surface antigen assay, the analyte-chemiluminescent conjugate complex is separated from unreacted chemiluminescent conjugate. In a competitive assay, the reactant-chemiluminescent conjugate complex is separated from unreacted chemiluminescent conjugate. In a sequential saturation assay and in a competitive displacement assay, the reactant-chemiluminescent conjugate complex is separated from unreacted chemiluminescent conjugate. Alternatively, in homogeneous assays the reaction products are not separated. After the assay reagents have been allowed to react, the chemiluminescence may be measured from the whole assay mixture whether such mixture is in solution, on a solid phase or distributed between various membrane layers of a dip stick or other solid support. The glucose assay using glucose oxidase and a chemiluminescent moiety illustrates a simple homogeneous assay in which separation is unnecessary. The quenching assay illustrates a more complex homogeneous assay in which separation is unnecessary.

Finally, "measuring the chemiluminescence" shall include, where relevant, the act of separating those specific binding reaction products, the formation of which are proportional to the presence of analyte in the sample, from other reaction products. It shall also include, where relevant, the acts of (i) treating the chemiluminescent moiety with acid to cleave an acid labile group from the moiety, and/or (ii) triggering the chemiluminescent moiety to chemiluminesce in the case of those assay formats in which the formation of the reaction products does not itself trigger the chemiluminescent moiety.

In accordance with yet another aspect of the present invention, there are provided chemiluminescent assay kits comprising a conjugate as described herein. Such kits preferably comprise one or more assay components as described above, including at least one chemiluminescent assay component comprising chemiluminescent moiety of the invention, and may optionally include one or more of: instructions for performing the detection; reagents, such as buffers, for use in performing the detection; pipets for liquid transfers; etc.

The invention will now be described in greater detail by reference to the following non-limiting examples.

EXAMPLE 1

Preparation of Hydrophilic Chemiluminescent Acridinium Labeling Reagents

The relatively hydrophobic compound MeAE [2,6-(dimethyl)-3-chlorosulfonylphenyl-N-methyl-acridinium-9-carboxylate triflate] was prepared from 2,6-(dimethyl)phenylacridine-9-carboxylate by N-methylation with methyl triflate followed by reaction to form the sulfonyl chloride [U.S. Pat. No. 5,284,952]. This compound was converted to hydrophilic acridinium esters by reaction with a hydrophilic amino acid or peptide followed by formation of the N-hydroxysuccinimide (NHS) or pentafluorophenyl (PFP) ester according to the scheme in FIG. 1. The synthesis of exemplary compounds is described in additional detail below.

EXAMPLE 2

MeAE-PEO4-NHS

MeAE-PEO4-NHS

To a stirred solution of 130 mg (0.34 millimole) tetraethyleneglycol amino propionic acid, TFA and 190 mg (1.4 millimole) diisopropylethylamine in 4 ml dry acetonitrile was added three portions of MeAE in dry DMF [total amount=100 mg (0.17 millimole) in 1.5 ml]. The mixture was stirred in the dark under argon at room temperature for 2.5 hrs. The mixture was acidified by addition of 2 M aqueous trifluoroacetic acid to pH 3 on a wet pH strip. The volatiles were removed on a rotary evaporator and then the residue was redissolved in 10% acetonitrile-90% aqueous 50 mM acetic acid. The mixture was passed through a Sephadex G10 gel filtration column using 10% acetonitrile/90% aqueous 50 mM acetic acid as eluting solvent. The amount of product was 47.5 micromole (28% yield) as determined by UV-vis absorbance. The solution collected from the gel filtration was acidified to pH 2 by addition of 2 M aqueous methanesulfonic acid. The volatiles were removed by vacuum to produce the yellow solid MeAE-PEO4-COOH. ESI mass spec. Positive mode m/z=669 (acridinium ion carboxylic acid), m/z=691 (sodium salt). Negative mode m/z=781 (acridinium trifluoroacetate carboxylate).

The MeAE-PEO4-COOH was dried by azeotropic evaporation with 1 ml pyridine followed by vacuum dessication. To a solution of 48 micromole MeAE-PEO-COOH and 0.52 millimole pyridine in 0.5 ml dry DMF was added 61 mg (0.24 millimole) solid disuccinimidyl carbonate. The reaction was allowed to proceed for 6 hrs with stirring at room temperature under argon. Dry ether (5 ml) was added to precipitate the MeAE-PEO4-NHS product. The supernatant was removed by aspiration and then the solid was redissolved in DMF, reprecipitated by addition of ether, washed with ether and dried. ESI mass spec. Positive mode m/z=766 (acridinium ion NHS ester).

EXAMPLE 3

MeAE-HCA-NHS

MeAE-HCA-NHS

A mixture composed of 293 mg (1.6 mmole) homocysteic acid, 0.5 ml water, 2.8 ml of 1 M NaOH, 4 ml of 0.2 M carbonate buffer pH 9.3 and 1 ml DMF was cooled externally in an ice bath. A freshly prepared solution of 40 mg (0.2 mmole) MeAE in 0.5 ml DMF was added with stirring. More carbonate buffer pH 9.3 (3 ml of 0.2 M) was added. Another portion of freshly prepared MeAE (40 mg (0.2 mmole) in 0.5 ml DMF) was added to the stirred cooled mixture. Carbonate buffer pH 9.3 (0.5 ml of 0.2 M) and DMF were added to the stirred mixture. The mixture was stirred in the ice bath for 30 min and then at room temperature for 30 min. The mixture was acidified to pH 2 by addition of 1 M aqueous methanesulfonic acid. After removal of volatiles on a rotary evaporator, the product was extracted from the solid residue into three 20-ml portions of hot methanol. The methanol extract was filtered and then concentrated to dryness to produce a yellow solid. The solid was recrystallized twice by dissolving in hot methanol followed by addition of ethyl acetate to produce 92 mg (78% yield) of MeAE-HCA product. ESI negative mode using DMSO/MeCN as solvent: m/z=603 (pseudobase sulfonate anion). Negative mode using MeOH/H$_2$O as solvent: m/z=617 (methoxy adduct sulfonate anion), m/z=308 (methoxy adduct sulfonate carboxylate dianion).

Trifluoroacetic acid in acetonitrile (2 ml of 2 M solution) was added to solid MeAE-HCA (25 mg, 43 micromole) to convert the pseudobase to acridinium. The volatiles were removed in vacuum and then the yellow solid was dried in vacuum for 2 hrs. A mixture of the dry MeAE-HCA, 41 µl pyridine 0.51 mmole) and 66 mg (0.26 mmole) disuccinimidyl carbonate was stirred under argon at room temperature for 5 hrs. Ether (10 ml) was added to precipitate the product and then the supernatant was removed by aspiration. The product was dried in vacuum, redissolved in 1.5 ml DMF, reprecipitated by addition of 6 ml ether, collected and dried in vacuum. The ether precipitation was repeated to produce 31.7 mg (100%) of MeAE-HCA-NHS product. ESI mass spec, positive mode: m/z=684 (acridinium NHS ester sulfonic acid), m/z=706 (acridinium NHS ester sodium sulfonate).

EXAMPLE 4

C. MeAE-Gly2-NHS

MeAE-Gly2-NHS

A mixture of glycylglycine (264 mg, 2 mmole), water (1 ml), 1.8 ml of 1 M NaOH, 4 ml of 0.2 M carbonate buffer pH 9.3 and 1 ml DMF was cooled externally in an ice bath. Three aliquots of freshly prepared solution of MeAE (total amount=120 mg (0.20 millimole) in 3 ml DMF) were added with stirring. After stirring for 30 min in the ice bath, 1 M aqueous methanesulfonic acid was added to acidify the mixture to pH 2.5. The volatiles were removed in vacuum and then the product was extracted from the yellow solid by treatment with three 15-ml portions of hot 2-propanol. The solution was filtered and concentrated to dryness to produce 123 mg of yellow solid. The solid was recrystallized from hot 2-propanol-ethyl acetate to produce 32 mg (25% yield) of MeAE-Gly2 product. ESI mass spec, positive mode: m/z=536 (acidinium carboxylic acid), m/z=558 (acridinium sodium carboxylate), m/z=590 (acridinium potassium carboxylate).

A mixture of 20 mg (32 micromole) MeAE-Gly2, 30 µl (0.3 mmole) pyridine and 49 mg (0.19 mmole) disuccinimidyl carbonate in 0.8 ml dry DMF was stirred in the dark overnight at room temperature under argon. The volatiles were removed in vacuum and then the residue was redissolved in 0.5 ml dry DMF and then the product was precipitated by addition of 3 ml dry ether. After drying in vacuum, the steps of dissolving in DMF, precipitating with ether and drying in vacuum were repeated three times to produce 8.7 mg (37% yield) of MeAE-Gly2-NHS product. ESI mass spec, positive mode: m/z=633 (NHS acridinium ion).

EXAMPLE 5

MeAE-Gly3-NHS

MeAE-Gly3-NHS

A mixture composed of 96 mg (0.51 mmole) triglycine, 4 ml 0.5 M carbonate buffer pH 9.5, and 1 ml DMF was cooled externally in an ice bath. Three aliquots of freshly prepared solution MeAE in DMF (total amount=100 mg (0.17 mmole) in 1.5 ml) were added with stirring five minutes apart. The mixture was stirred for 15 min in the cold and 30 min at room temperature. The mixture was acidified to pH 2.5 by addition of 2 M aqueous methanesulfonic acid and then concentrated to dryness to produce a yellow solid. The product was extracted with three 40-ml portions of 2-propanol, filtered and concentrated to dryness. The 2-propanol extraction was repeated to produce 96 mg (80% yield) of yellow solid MeAE-Gly3 product. ESI mass spec, positive mode: m/z=593 (acridinium carboxylic acid).

A mixture composed of 47 mg (67 micromole) MeAE-Gly3, 64 µl (0.79 mmole) of pyridine and 103 mg (0.40 mmole) disuccinimidyl carbonate in 2 ml dry DMF was stirred for 5 hr in the dark at room temperature under argon. The product was isolated by ether precipitation following the same procedure as in the MeAE-Gly2-NHS preparation to produce 23.9 mg (45% yield) of MeAE-Gly3-NHS product. ESI mass spec, positive mode: m/z=690 (acridinium NHS ester).

EXAMPLE 6

SPAE

The compound SPAE [2,6-(dimethyl)-3-chlorosulfonylphenyl-N-(3-sulfopropyl)-acridinium-9-carboxylate] is a hydrophilic acridinium ester and has the following structure:

SPAE

Figure 2:
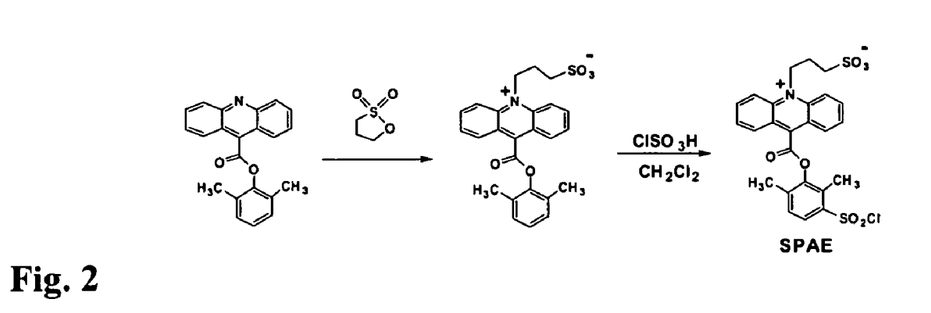
FIG. 2 provides a reaction scheme for preparation of 2,6-(dimethyl)-3-chlorosulfonylphenyl-N-(3-sulfopropyl)-acridinium-9-carboxylate ("SPAE").

This compound was synthesized from 2,6-(dimethyl)phenylacridine-9-carboxylate according to the scheme in FIG. 2. The synthesis of this compound is described in additional detail below.

2,6-Dimethylphenyl 9-acridinecarboxylate (0.654 g, 2.0 mmole) and molten 99+% 1,3-propane sultone (2.4 g, 20 mmole) was placed in an oven-dried 20-ml glass vial. The mixture was microwaved at 70% power in a Sanyo Carousel Model R-230-BK microwave oven for two 15-second periods followed by one 10-second period with swirling between microwaving periods. Total microwaving time=40 seconds. To hydrolyze sulfonate ester groups, 5 ml of 50% methanol, 50% aqueous 0.2 M hydrochloric acid was added and then the black mixture was heated with magnetic stirring in a 80° C. oil bath for 5 hours. The product was purified by preparative HPLC through a 250 mm×21.2 mm Phenomenex Luna 5 micron C18(2) column using isocratic mobile phase with 60% A and 40% B at 8 ml/min flow rate. (Solvent A=0.1% aqueous trifluoroacetic acid, Solvent B=acetonitrile). For each of 30 chromatographic runs, 200 microliters of sample was injected. The product with a retention time between 14 to 15 min was collected when the absorbance at 430 nm was greater than 0.2. The combined collected 14-15 min fraction was concentrated to dryness on a rotary evaporator to produce 0.49 g of yellow solid. The 2,6-(Dimethyl)phenyl-N-(3-sulfopropyl)acridine-9-carboxylate product was recrystallized from hot 1:1 acetonitrile/methanol with addition of ethyl acetate to produce 401 mg of crystals. The mother liquor was concentrated to produce a second crop (76 mg). Yield=53%. ESI mass spec in methanol. Positive mode: m/z=450 (acridinium sulfonic acid) and 472 (acridinium sodium sulfonate). Negative mode: m/z=480 (methoxy adduct sulfonate anion) and 466 (pseudo base sulfonate anion). UV-visible spectrum in 100 mM phosphate pH 2.0: $\lambda_{max}$=370 and 430 nm.

To a stirred suspension of 2,6-(dimethyl)phenyl-N-(3-sulfopropyl)acridine-9-carboxylate (180 mg, 0.40 mmole) in 12 ml dry dichloromethane in a 25-ml oven-dried flask under argon, was added 400 microliters of 99+% chlorosulfonic acid (0.70 g, 6.0 mmole). The chlorosulfonation was allowed to proceed overnight under argon at room temperature. The small amount of insoluble brown solid was allowed to settle and then the yellow supernatant was added dropwise from a Pasteur pipet to a flask containing stirred 100 ml of anhydrous ether under argon. The product was collected on a sintered glass funnel under a blanket of argon under a large inverted funnel and then washed with about 30 ml of dry ether. The yellow solid SPAE product (212 mg, 97% yield) was dried overnight in vacuum over phosphorus pentoxide. ESI mass spec in methanol. Positive mode: m/z=548 and 550 (acridinium sulfonyl chloride). Negative mode: m/z=578 and 580 (sulfonyl chloride methoxy adduct sulfonate anion). UV-visible spectrum in 100 mM phosphate pH 2.0: $\lambda_{max}$=371 and 431 nm (acridinium ion). UV-visible spectrum in 100 mM carbonate pH 9.6: $\lambda_{max}$=287 and 320 nm (pseudo base). Specific chemiluminescence activity in 0.4% BSA in phosphate buffer pH 6.0 using the Berthold chemiluminometer=3.8×10 relative luminescence units per mole.

EXAMPLE 7

F. SPAE-PEO4-PFP

The hydrophilicity of SPAE can be further enhanced by attachment to a linker such as a hydrophilic amino acid or peptide followed by conversion to the NHS or PFP ester. For example, SPAE-PEO4-PFP was prepared which has the following structure:

SPAE-PEO4-PFP

A freshly prepared solution of 5.8 mg (10.6 micromole) SPAE in 0.5 ml anhydrous methanol was added to a stirred solution of 32 mg (82 micromole) of tetraethylene glycol amino propionic acid and 32 μl (0.18 mmole) of diisopropylethylamine in 0.2 ml methanol. The reaction was allowed to proceed for 1 hr in the dark at room temperature under argon. The mixture was acidified by addition of 20 μl of glacial acetic acid and then concentrated to 0.2 ml. Water (0.4 ml) was added and then the product was purified by HPLC through a 10 mm×250 mm Phenomenex Luna C18(2) column using a linear gradient of acetonitrile with absorbance monitoring at 360 nm. Gradient program: 10% B for 2 min, 10% to 90% B in 16 min, 90% B for 3 min, 90% B to 10% B in 1 min, 10% B for 2 min. (Solvent A=0.1% trifluoroacetic acid, Solvent B=acetonitrile). The fraction with retention time of 16 min contained the SPAE-tetraethylene glycol propionic acid (3.2 micromole based on UV-vis spectrum (30% yield). ESI mass spec, positive mode: m/z=777 (acridinium sulfonic acid carboxylic acid), m/z=799 (acridinium carboxylic acid sodium sulfonate). Negative mode: m/z=807 (methoxy adduct sulfonate anion), m/z=403 (methoxy adduct sulfonate carboxylate dianion).

A mixture of SPAE-tetraethylene glycol propionic acid (0.77 micromole), 2.66 μl (15.5 micromole) of pentafluorophenyl trifluoroacetate and 1.3 μl (16 micromole) pyridine in 0.2 dry DMF was stirred in the dark at room temperature under argon for 1 hr. The reaction mixture was distributed into four vials and then the volatiles were removed in vacuum to produce SPAE-PEO4-PFP. ESI mass spec. Positive mode: m/z=943 (acridinium PFP ester sulfonic acid), m/z=965 (acridinium PFP ester sodium sulfonate). Negative mode: m/z=973 (PFP ester methoxy adduct sulfonate anion).

EXAMPLE 8

SPAE-(Lys-HCA)$_5$-PFP

Figure 3:
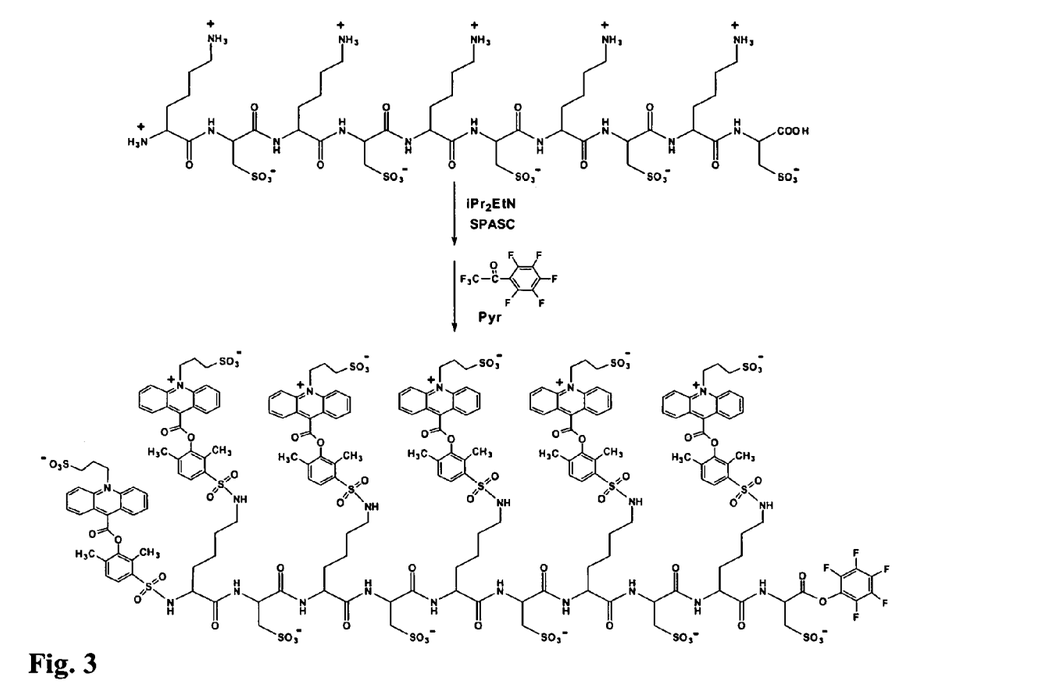
FIG. 3 provides a reaction scheme for preparation of SPAE-(Lys-HCA)$_5$-PFP.

Signal amplification can be achieved by the use of a hydrophilic peptide linker that can carry several acridinium labels attached to pendant groups on the peptide backbone. This peptide amplifier can also carry several sulfonate groups at regular intervals for improved aqueous solubility and an amine-reactive functional group for covalent attachment to proteins. One advantage of such labeling strategy is that high specific chemiluminescence activity can be achieved while keeping most of the lysines intact to preserve immunoaffinity. An example of such amplifier is SPAE-(Lys-HCA)$_5$-PFP. A synthesis for this exemplary molecule is provided schematically in FIG. 3, and in additional detail below.

The amplifier peptide SPAE-(Lys-HCA)$_5$ was prepared by the reaction between the synthetic peptide Lys-HCA-Lys-HCA-Lys-HCA-Lys-HCA-Lys-HCA (HCA=homocysteic acid) and excess SPAE (>10 moles SPAE per mole of peptide) in the presence of a base such as diisopropylethylamine. The resulting multi-acridinium peptide carboxylic acid was purified by gel filtration and then treated with excess pentafluorophenyl trifluoroacetate to produce the amine-reactive PFP ester.

EXAMPLE 9

Preparation of Acridinium-Protein Conjugates

Figure 4:
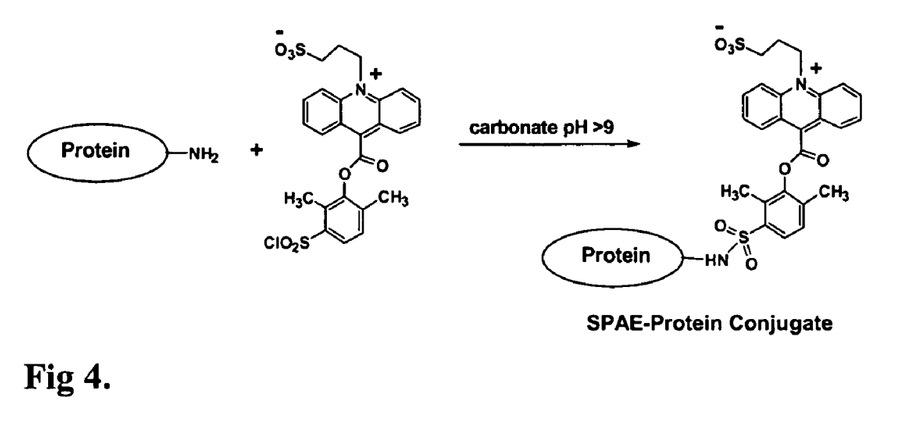
FIG. 4 provides a reaction scheme for preparation of exemplary acridinium-protein conjugates according to the invention.

The chemiluminescent compounds of the present invention can be reacted with specific binding partner such as an antibody, antibody fragment, avidin or streptavidin, protein A or protein G, oligonucleotide, ligand, or hapten. A sulfonyl chloride group reacts readily with lysine or the terminal amino group of proteins in aqueous or mixed aqueous/organic buffered solution, typically at pH>9 to produce stable sulfonamide linkages as shown in the scheme in FIG. 4. The following exemplary procedure used to label anti-TSH with SPAE is generally applicable for preparing the acridinium-antibody conjugates using sulfonyl chloride reagents/

In preparation for conjugation using SPAE, 1 mg (6.7 nanomole) of goat anti-TSH tag antibody was buffer-exchanged in an Amicon Centricon concentrator cartridge (MW cut-off=30,000) to produce a solution of 1 mg antibody in 400 μl of 100 mM carbonate pH 9.6. In a typical conjugation, the labeling reagent (7 μl of freshly prepared 22.8 mM SPAE (MW=547) in dry DMF, as determined by UV-vis absorbance at 368 nm, was added and then the mixture was shaken. The conjugation reaction was allowed to proceed for 30 minutes at room temperature with occasional shaking. The conjugate was purified by gel filtration though a 27 cm×1 cm column containing 2:1 bed volume of Sephadex G-75 and Sepharose 6B. The column was eluted with 100 mM phosphate pH 6.0 containing 150 mM NaCl with monitoring of UV absorbance at 280 nm. The fractions with elution times of 12 min, 18 min and 32 min contained the antibody aggregate, the antibody-SPAE conjugate and the hydrolyzed excess labeling reagent, respectively. The protein recovery based on Coomasie Blue colorimetric protein assay was 73%. The UV-vis spectrum of an aliquot of the conjugate fraction acidified to pH 2 was recorded to determine the number of acridinium labels per IgG molecule. Based on the acridinium and protein absorbances at 368 nm ($\epsilon$=15,700 M$^{-1}$ cm$^{-1}$) and 280 nm (extinction coefficient=1.35 O.D. for a 1 mg/ml solution), respectively, the conjugate was estimated to contain 2.6 labels per IgG molecule. The specific chemiluminescence activity for this conjugate measured using the Berthold Chemiluminometer was 743 RLU/pg.

Figure 5A:
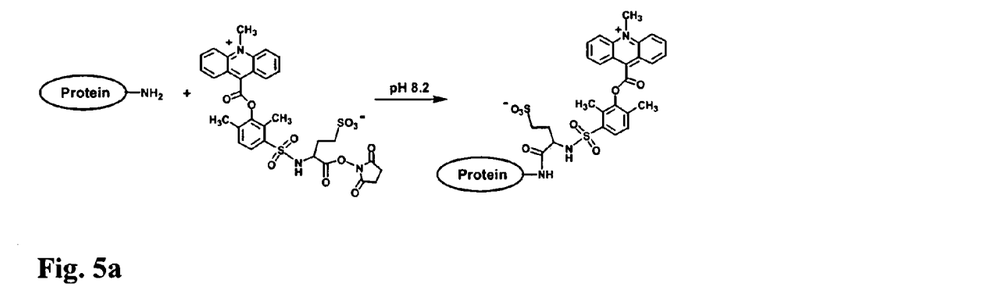
Figure 5B:
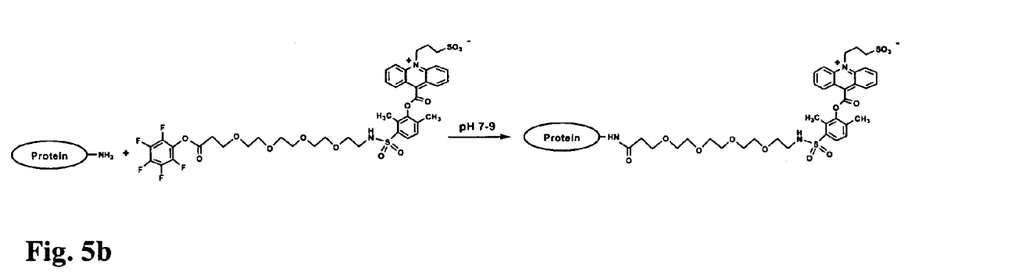

The NHS ester activated acridinium compounds react with amino groups of proteins in aqueous solution in the pH range 7-9 to produce stable amide linkages as shown in the scheme in FIG. 5a. In a similar manner, the pentafluorophenyl ester group reacts with amino groups of proteins in aqueous buffered solution typically at pH 7-8 to produce bioconjugates with the label attached via stable amide linkages as shown in the scheme in FIG. 5b. The following procedure was used to prepare exemplary conjugates with the NHS or PFP activated acridinium derivatives:

EXAMPLE 10

Preparation of Conjugates Using Acridinium-NHS Reagents

In a typical conjugation reaction, 1.5 mg of goat polyclonal ant-TSH antibody was buffer-exchanged twice on a 30,000 MW cutoff Amicon Centricon concentrator with 20 mM phosphate buffer pH 7.8 to produce 600 uL of 2.5 mg/ml antibody solution. MeAGly2-NHS (66 uL of 2.27 mM soln based on UV-vis absorbance) was added to produce a 15× reagent/antibody molar ratio. The conjugation was allowed to proceed for 1 hr at room temperature with occasional mixing. The conjugate was purified by gel filtration through a mixed bed column in the same manner as the SPAE conjugates. The recovery based on UV absorbance was 87%. The conjugate was found to contain 1.4 acridinium labels per antibody based on UV-vis absorbance.

EXAMPLE 11

Preparation of Conjugates Using Acridinium-PFP Reagents

Goat polyclonal anti-TSH antibody (1.12 mg) was buffer-exchanged twice to produce 450 uL of 2.5 mg/mL antibody solution in 100 mM phosphate pH 7.4. Freshly prepared SPAE-PEO-PFP in dry acetonitrile (40 uL of 4.2 mM solution based on UV-vis absorbance) was added with mixing to produce a 22× reagent/antibody molar ratio and then the conjugation was allowed to proceed for 1 hr at room temperature in the dark. The reaction was quenched by addition of 10 uL of 1 M glycine in water and then the mixture was chromatographed through the mixed bed gel filtration column in the same manner as the SPAE conjugates. The specific chemiluminescence activity was 332 RLU/pg.

EXAMPLE 12

Analysis of Conjugates

The anti-TSH and anti-ACTH were labeled with the hydrophilic acridinium compounds at various molar ratios. The protein recovery was determined by Coomasie Blue calorimetric protein assay. The results are summarized below. Compared to the relatively hydrophobic MeAE compound, the hydrophilic labels gave much higher protein recovery. Very high levels of acridinium labeling were achieved with the hydrophilic labels.

TABLE 1

TSH Goat Polyclonal Ab Conjugates

|  | Labeling Ratio | % Recovery |
| --- | --- | --- |
| MeAE | 26X | 17 |
| MeAE-Gly2-NHS | 65X | 41 |
| MeAE-Gly3-NHS | 46X | 49 |
| MeAE-Gly4-NHS | 26X | 72 |
| MeAE-HCA-NHS | 72X | 108 |
| SPAE | 13X | 104 |
| SPAE | 17X | 91 |
| SPAE | 21X | 82 |
| SPAE | 24X | 73 |
| SPAE | 32X | 53 |
| SPAE | 36X | 55 |
| SPAE | 46X | 34 |

TABLE 2

ACTH Monoclonal Ab Conjugates

|  | Labeling Ratio | % Recovery |
| --- | --- | --- |
| MeAE | 5X | 58 |
| SPAE | 5X | 72 |
| SPAE | 9X | 78 |
| SPAE | 14X | 86 |

Assay Results

The assays were run on a Nichols Advantage Specialty System with Nichols Advantage assay wash and triggers. The assay results were generated using the magnetic particles, biotinylated antibodies, buffers and standards from commercially available Nichols Advantage Immunoassay kits.

TSH Assay Protocol
1. Pipette 25 uL of a solution containing biotinylated monoclonal anti-TSH and acridinium labeled polyclonal goat anti-TSH.
2. Pipette 200 uL of patient sample.
3. Incubate for 20 minutes at 37°
4. Pipette 50 uL of assay buffer and 13 uL of streptavidin coated magnetic particles.
5. Incubate for 10 minutes at 37°.
6. Wash 3× with assay wash.
7. Trigger and count (2 sec.).

ACTH Assay Protocol
1. Pipette 70 uL of biotinylated monoclonal anti-TSH.
2. Pipette 20 uL of acridinium labeled monoclonal anti-TSH.
3. Pipette 150 uL of patient sample or standard/
4. Incubate for 20 minutes at 37°
5. Pipette 20 uL of streptavidin coated magnetic particles and 150 uL of buffer.
6. Incubate for 10 minutes at 37°.
7. Wash 3× with assay wash.
8. Trigger and count (2 sec.).

Because the high acridinium labeling was achieved with the hydrophilic acridinium esters, less antibody was required in the assay. The amount of tracer antibody used was decreased by a factor of 2 for the TSH assay and a factor of 3 for the ACTH assay. Even with significantly less antibody, the hydrophilic acridinium ester labeled antibodies gave improved standard curves with higher signal to noise observed at all standard levels.

The analytical sensitivity (limit of detection) was determined by reading the +2SD response from n=20 replicate measurements of the zero standard from the standard curve. The analytical sensitivity of the both the TSH and ACTH assays was significantly improved using the relatively hydrophilic acridinium labeled antibodies at a lower antibody concentration than the relatively hydrophobic acridinium (MeAE) labeled antibody.

TABLE 3

TSH Assay Standard Curve and Analytical Sensitivity

| STD | TSH Conc. uIU/mL | 0.4 ug/mL 24X SPAE RLU | 0.8 ug/mL 24X MeAE RLU |
| --- | --- | --- | --- |
| 0 | 0 | 385 | 343 |
| 1 | 0.014 | 669 | 520 |
| 2 | 0.021 | 906 | 651 |
| 3 | 0.048 | 1632 | 1045 |
| 4 | 0.49 | 13111 | 7541 |
| 5 | 2.6 | 54164 | 30449 |
| 6 | 4.6 | 96720 | 56068 |
| 7 | 9.5 | 164203 | 93869 |
| 8 | 19 | 282692 | 166464 |
| 9 | 51 | 487052 | 310816 |
| Analytical Sensitivity (uIU/mL) |  | 0.0018 uIU/mL | 0.0031 uIU/mL |

TABLE 4

ACTH Assay Standard Curve and Analytical Sensitivity

| STD | ACTH Conc. pg/mL | 0.2 ug/mL 5X SPAE RLU | 0.6 ug/mL 5X MeAE RLU |
| --- | --- | --- | --- |
| 0 | 0 | 507 | 436 |
| 1 | 3.4 | 928 | 624 |
| 2 | 10.3 | 1943 | 1035 |
| 3 | 36 | 5512 | 2438 |

TABLE 4-continued

ACTH Assay Standard Curve and Analytical Sensitivity

| STD | ACTH Conc. pg/mL | 0.2 ug/mL 5X SPAE RLU | 0.6 ug/mL 5X MeAE RLU |
|---|---|---|---|
| 4 | 110 | 15590 | 6441 |
| 5 | 355 | 55645 | 22393 |
| 6 | 1160 | 172923 | 73275 |
| Analytical Sensitivity (uIU/mL) | | 0.29 pg/mL | 0.73 pg/mL |

Unless otherwise defined, all technical and scientific terms used herein have the same meanings as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

While the invention has been described in detail with reference to certain preferred embodiments thereof, it will be understood that modifications and variations are within the spirit and scope of that which is described and claimed.

What is claimed is:

1. A chemiluminescent compound having the structure:

wherein:
X=O, S or NR', wherein R' is H, alkyl or substituted alkyl;
Y=O or S;
Z=alkyl, sulfoalkyl, alkenyl, or sulfoalkenyl;
Ar=aryl or heteroaryl bearing at least one —SO$_2$—NH-Q substitutent, wherein Q is a polyoxyalkylene linker bearing a free amine reactive group;
R=sulfoalkyl or sulfoalkenyl;
when Z is alkyl or alkenyl, A$^-$ is present and is a suitable counter-ion, and when Z is sulfoalkyl or sulfoalkenyl, A$^-$ is not present; and
n=0-3.

2. A compound according to claim 1 wherein X is O.

3. A compound according to claim 1 wherein Y is O.

4. A compound according to claim 1 wherein Z has the structure:

—(CR"$_2$)$_q$—SO$_3^-$, wherein:
each R" is independently H, lower alkyl or substituted lower alkyl; and
q=1-6.

5. A compound according to claim 4 wherein Z is sulfopropyl.

6. A compound according to claim 1 wherein Z has the structure:

—(CR"$_2$)$_r$—C(R")═C(R")—(CR"$_2$)$_r$—SO$_3^-$, wherein:
each R" is independently H, lower alkyl or substituted lower alkyl; and
each r is independently 0-4.

7. A compound according to claim 1 wherein Ar is aryl.

8. A compound according to claim 7 wherein said aryl is 2,6-dialkyl substituted.

9. A compound according to claim 8 wherein Ar has the structure:

10. A compound according to claim 1 wherein Ar is heteroaryl.

11. A compound according to claim 10 wherein said heteroaryl is a pyridyl, pyrimidyl, pyrazinyl, triazolyl, isooxazolyl, isothioazolyl, or imidazolyl.

12. A compound according to claim 1 wherein the amine reactive group is a succinimidyl ester, N-hydroxyphthalimide ester, pentafluorophenyl ester, tetrafluorophenyl ester, 2-nitrophenyl ester, 4-nitrophenyl ester, dichlorotriazine, or isothiocyanate.

13. A compound according to claim 1 that is 2,3,4,5,6-pentafluorophenyloxy-1-carbonyl-4,7,10,13-tetraoxapentadecyl-(15-amino)-3'-sulfonyl-2',6'-dimethylphenyl-N-(3-sulfopropyl)-acridinium-9-carboxylate or [2,5-dioxo-(1-pyrrolidinyl)oxy]-1-carbonyl-4,7,10,13-tetraoxapentadecyl-(15-amino)-3'-sulfonyl-2',6'-dimethylphenyl-N-methyl-acridinium-9-carboxylate.

14. A chemiluminescent conjugate comprising a chemiluminescent compound according to claim 1 conjugated with a specific binding material.

15. A conjugate according to claim 14 wherein said specific binding material is an antibody.

16. A chemiluminescent assay kit comprising a conjugate according to claim 15.

17. An assay for the presence of an analyte in a sample, said assay comprising:
contacting an analyte with a conjugate according to claim 14, wherein said conjugate specifically binds to the analyte,
inducing chemiluminescence of the conjugate specifically bound to the analyte in the presence of a peroxide or molecular oxygen, and
measuring chemiluminescence therefrom to assay the presence of the analyte.

* * * * *